(12) United States Patent
Ogura

(10) Patent No.: US 9,644,998 B2
(45) Date of Patent: May 9, 2017

(54) TESTING ELEMENT, TESTING APPARATUS, AND TESTING SYSTEM

(75) Inventor: Masaya Ogura, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 792 days.

(21) Appl. No.: 14/113,171

(22) PCT Filed: Apr. 6, 2012

(86) PCT No.: PCT/JP2012/060089
§ 371 (c)(1),
(2), (4) Date: Oct. 21, 2013

(87) PCT Pub. No.: WO2012/147536
PCT Pub. Date: Nov. 1, 2012

(65) Prior Publication Data
US 2014/0052400 A1    Feb. 20, 2014

(30) Foreign Application Priority Data

Apr. 28, 2011 (JP) .................................. 2011-100981

(51) Int. Cl.
*B01L 3/00* (2006.01)
*G01D 18/00* (2006.01)
(Continued)

(52) U.S. Cl.
CPC ............ *G01D 18/008* (2013.01); *B01L 3/545* (2013.01); *G01N 33/48771* (2013.01);
(Continued)

(58) Field of Classification Search
CPC ...................................................... B01L 3/545
(Continued)

(56) References Cited

U.S. PATENT DOCUMENTS

| | | |
|---|---|---|
| 6,385,497 B1 | 5/2002 | Ogushi et al. |
| 6,892,109 B2 | 5/2005 | Ogushi et al. |

(Continued)

FOREIGN PATENT DOCUMENTS

| | | |
|---|---|---|
| JP | 2001-229291 A | 8/2001 |
| JP | 2002-340906 A | 11/2002 |

(Continued)

OTHER PUBLICATIONS

Japanese Office Action dated May 7, 2015 in corresponding Japanese Patent Application No. 2011-100981 (with whole English translation).

(Continued)

*Primary Examiner* — Bryan Bui
(74) *Attorney, Agent, or Firm* — Fitzpatrick, Cella, Harper & Scinto

(57) ABSTRACT

Conventional laboratory tests require calibration before each test. This results in the need for a reagent for calibration before each test. Additionally, calibration takes a long time, and the total TAT (Turn Around Time) of a testing system increases. The testing system thus suffers from the difficulty of improving the testing efficiency. This invention, which has been made to solve the problem, provides a testing element for performing a laboratory test, wherein the testing element includes an information recording section at the surface of and/or inside the testing element, and the information recording section stores information on a characteristic of the testing element.

9 Claims, 3 Drawing Sheets

(51) Int. Cl.
   *G01N 33/487* (2006.01)
   *G01N 35/00* (2006.01)

(52) U.S. Cl.
   CPC ...... *G01N 35/00732* (2013.01); *B01L 3/5027* (2013.01); *B01L 2300/021* (2013.01); *B01L 2300/023* (2013.01); *G01N 35/00693* (2013.01); *G01N 2035/00811* (2013.01); *G01N 2035/00821* (2013.01)

(58) Field of Classification Search
   USPC .......................................................... 702/85
   See application file for complete search history.

(56) References Cited

U.S. PATENT DOCUMENTS

| | | | |
|---|---|---|---|
| 6,963,786 | B2 | 11/2005 | Ogushi et al. |
| 7,062,343 | B2 | 6/2006 | Ogushi et al. |
| 7,200,288 | B2 | 4/2007 | Ogura |
| 7,630,523 | B2 | 12/2009 | Ogura |
| 7,805,279 | B2 | 9/2010 | Ogushi et al. |
| 7,883,015 | B2 | 2/2011 | Ackermann et al. |
| 2005/0169797 | A1* | 8/2005 | Oshima ................ B01J 19/0046 422/50 |
| 2007/0013733 | A1 | 1/2007 | Katsurai et al. |
| 2008/0217407 | A1* | 9/2008 | Ackermann ........ G06F 19/3412 235/439 |
| 2014/0016007 | A1 | 1/2014 | Ogura et al. |

FOREIGN PATENT DOCUMENTS

| | | |
|---|---|---|
| JP | 2003-279583 A | 10/2003 |
| JP | 2006-164295 A | 6/2006 |
| JP | 2007-24656 A | 2/2007 |
| JP | 2008-537128 A | 9/2008 |
| JP | 2009-128277 A | 6/2009 |
| JP | 2009-229264 A | 10/2009 |
| JP | 2010-8100 A | 1/2010 |
| JP | 2010-197235 A | 9/2010 |
| WO | 2006/009251 A1 | 1/2006 |

OTHER PUBLICATIONS

Japanese Office Action dated Jan. 5, 2016 in Japanese Patent Application No. 2011-100981.

International Preliminary Report on Patentatbility dated Nov. 7, 2013 in corresponding PCT Patent Application No. PCT/JP2012/060089.

* cited by examiner

TESTING ELEMENT, TESTING APPARATUS, AND TESTING SYSTEM

TECHNICAL FIELD

The present invention relates to a testing system, a testing apparatus, and a testing element for performing a laboratory test and, for example, to a testing system, a testing apparatus, and a testing element used in, e.g., a medical test such as a genetic test or a protein test, testing of an agricultural product or an organism, or testing of a substance in an environment.

BACKGROUND ART

Conventional laboratory tests require reagents of the order of microliters to milliliters for chemical analysis, reagent preparation, chemical synthesis, and reaction detection. Production of a reaction field finer than a test tube by applying lithography process technology or thick film process technology has recently enabled testing using a reagent of the order of nanoliters. μ-TAS (Micro-Total Analysis System) technology is a technology for applying a laboratory test using such a fine reaction field to, e.g., medical test and diagnosis including a genetic test, a chromosomal test, and cytoscopy, biotechnology, testing of a trace amount of substance in an environment, and investigation of the breeding environment of an agricultural product and the like and testing of the genes of an agricultural product. In a conventional laboratory test, a reagent is mainly handled through manipulation by a technologist. The process of a laboratory test is generally complicated and thus it requires expert operation of equipment. μ-TAS technology enables process simplification and ease of operation. μ-TAS technology is also expected to produce substantial benefits, such as automation, an increase in speed, an increase in fineness, a reduction in cost, an increase in the level of promptness, and a reduction in environmental impacts.

In particular, in the field of medical tests, a testing system including a plurality of testing apparatuses connected over a network is used to enable sharing of information between pretreatment and a plurality of analyses, to facilitate management of a large number of specimens to be treated, or to achieve an increase in the speed of a laboratory test. In a medical testing system, medical testing elements using, e.g., μ-TAS technology described above is used as functional devices of a medical testing apparatus. In such a testing system, each of the testing elements is often used differently.

SUMMARY OF INVENTION

Technical Problem

If an advanced testing system as described above comes into common use, management of pieces of information used by a testing apparatus and a testing element used in the testing system and the apparatus and element may become a problem.

The amounts of reagents used by μ-TAS technology are different in order of magnitude from the amounts of reagents used in conventional tests. For this reason, in a testing element using μ-TAS technology, a fine channel fluid path for handling a reagent in a structure and an active electric circuit for reacting a reagent are placed, and a unit for controlling the fluid path and circuit is further provided. Such elements have respective micro structures. Slight differences in characteristics of the elements may therefore significantly disrupt a final test result. Since fine control of an element and acquisition of accurate data are required especially in a medical setting or the like, it is necessary to acquire characteristics of testing elements used in a testing system and perform calibration work, such as adjustment of equipment and correction of results, prior to actual use.

The need for calibration before each test, however, results in the need for a reagent for calibration before each test. Calibration takes a long time, and the total TAT (Turn Around Time) of the testing system increases. Because of these factors, a conventional testing system using μ-TAS technology has difficulty in improving the testing efficiency.

Solution to Problem

To solve the above-described problem, the present invention proposes inclusion of a unit configured to measure a characteristic of a testing element in advance and recording the characteristic in the testing element. A testing apparatus reads out the recorded characteristic of the testing element, reads out a use condition previously saved in a table, and sets the read-out use condition in the testing apparatus. A testing system checks the read-out characteristic of the testing element against a database to see if the characteristic is a latest one and determines whether the use condition set in the testing apparatus is appropriate. The testing system compiles test results from a series of test apparatuses. The testing system then finely corrects a use condition for each testing element to an optimum use condition for a setting where the testing element is used and updates tables referred to by the testing apparatuses, by, e.g., statistically processing the compilation of the test results.

Advantageous Effects of Invention

The present invention eliminates the need for preliminary calibration of a testing element. Accordingly, an accurate test can be performed in a shorter time. Fine correction of a use condition for a testing apparatus to be used in various sites enables measurement of a use condition suitable for each setting and testing independent of disturbance conditions such as the temperature and atmospheric pressure of an installation site and vibrations.

Further features of the present invention will become apparent from the following description of exemplary embodiments with reference to the attached drawings.

DESCRIPTION OF EMBODIMENTS

Figure 1:
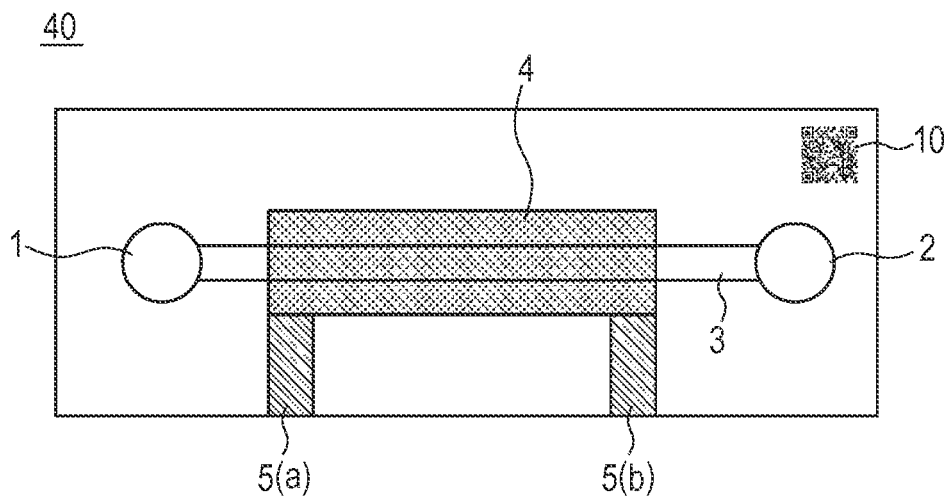
FIG. 1 illustrates a testing element according to a first embodiment of the present invention.

The present invention relates to a testing element, a testing apparatus, and a testing system which are used in a laboratory test. Examples of a laboratory test include tests which use, as a main analysis mechanism, a chemical reaction such as a biochemical reaction. The tests include, but are not limited to, a genetic test and a protein test.

A first aspect of the present invention relates to a testing element used in a laboratory test. A testing element according to the present invention includes an information recording section at the surface of and/or inside the testing element, and the information recording section stores information on a characteristic of the testing element.

Among testing elements used in testing apparatuses to detect values required for testing, there are many testing elements whose characteristics may change values to be detected. It is considered that these elements need to be calibrated before each use such that a value obtained by each element is equivalent to a value obtained by one of a reference measurement method and a measurement method specified by a vendor or the like.

A characteristic of a testing element here refers to a parameter specific to the element which may affect variations in measured values. Variations include an individual difference of an element generated during manufacture and an individual difference caused by a change with time and also include individual differences caused by sets of detection conditions, such as temperature, humidity, and reagent lot, and individual differences generated during use. Individual differences generated during manufacture include one generated during a manufacturing process and one generated during assembly. Many of the individual differences can be allowed for as margins of error at the time of designing while some are unavoidably generated. Individual differences caused by a change with time include one caused by vibrations during transport and also include one caused by oxidation with oxygen in the air, one caused by moisture absorption or drying resulting from humidity, and one caused by erroneous operation at the time of installation of a testing element. Since testing elements are used differently, objects to be considered as characteristics of the elements are different. For example, a characteristic in a first embodiment (to be described later) of this invention is a value of resistance used throughout a heater electrode system while a characteristic in a second embodiment (also to be described later) of this invention is dimensions, surface roughness, and the like related to the pressure resistance of a channel fluid path. The present invention is not limited to these. Any other parameter, such as a current value in electrochemical measurement, may be used as a characteristic of the testing element according to the present invention as long as the parameter serves as a factor causing variations in measured values from elements and it requires calibration. The above-described factors cause variations in measured values from individual elements. In a setting for a laboratory test, it is thus necessary to measure in advance how much a value obtained by an element deviates from a reference value and adjust (calibrate) a value obtained by actual measurement, at the time of each measurement.

In the present invention, the characteristic of an element is measured in advance as information on a characteristic and it is stored in the information recording section at the surface of and/or inside the testing element. By reading out a use condition and a result-correcting condition corresponding to the information on the characteristic of the element from a table prepared in advance and setting the conditions at the time of measurement, a measured value can be adjusted to an accurate value without the need of calibration before each measurement. The use condition is a condition for using the element and it is set so as to adjust the characteristic of the element. The result-correcting condition is a condition for correcting an obtained result according to the characteristic of the element. The conditions are prepared as control parameters in the table.

As the information recording section for storing the information on the characteristic of the element which is placed in the testing element according to the present invention, any unit can be adopted as long as a balance between the amount of information stored and the cost of the testing element is achieved. For example, a one-dimensional bar code or a two-dimensional bar code (e.g., a QR Code (registered trademark)) may be used. In addition to this, information may be recorded using a non-contact semiconductor memory device (a semiconductor chip which reads out information through wireless communication), such as an RF-IC or a FeliCa (registered trademark), and the information may be read out in a non-contact wireless manner. A manufacturing plant for the element, the date and time of manufacture, and the like may be recorded in the information recording section, in addition to the above-described information on the characteristic of the element which is measured in advance.

The present invention can be suitably used especially in a testing element which has a micro structure and which performs a laboratory test using a fine amount of reactant. Examples of such a testing element include a testing element which has a fine fluid path with a width of the order of micrometers formed so as to have a width of 1 µm to 900 µm, preferably 10 µm to 500 µm, and a depth of 10 µm to 1,000 µm, preferably 10 µm to 300 µm. The amount of reactant preferably falls within the range of 5 nl to 500 µl.

Alternatively, a testing element including a plurality of fluid paths and a plurality of heater electrodes for heating the interiors of the fluid paths can be used. Such a testing element can subject a reagent (containing a nucleic acid derived from a specimen) flowing in the fluid paths to temperature cycles for a PCR (Polymerase Chain Reaction) and thus it can be suitably used as an element for DNA analysis using a PCR. In this case, characteristics of the fluid paths may be stored as respective pieces of information in the information recording section.

A second aspect of the present invention relates to a testing apparatus for performing testing. When testing elements are set, a testing apparatus according to the present invention reads out information stored in an information recording section of each testing element with, e.g., an infrared reader and sets a use condition and a result-correcting condition for the element based on the read-out information on a characteristic of the testing element.

The testing apparatus according to the present invention includes a data record. The serial number of each testing element set in the testing apparatus, a characteristic of the element, a use condition, and a result when the element is used are recorded in the data record. Statistical processing of such results enables calculation of use conditions and result-correcting conditions with fewer errors for the respective testing elements.

Other pieces of information, such as test type, reagent used, and test date and time, may be stored in the data record. A result of a test performed under a read-out use condition is statistically processed, and items necessary for the test, such as test type, reagent type, and the amount of reagent, are saved. By accumulating the pieces of information in a table and giving feedback when performing a similar test, prompt and efficient testing can be performed.

Alternatively, it is also possible to record a manufacturing plant, the date and time of manufacture, and the like of the testing element and use the pieces of information to control variations generated during a manufacturing process. If the elapsed time to use of the testing element is calculated from the date of manufacture and a use date and recorded, the elapsed time can also be used to correct a result brought about by a change with time. The temperature, humidity, and atmospheric pressure of the installation environment of the apparatus, vibrations around the apparatus, and the like may be measured and may be stored together with a test result. This enables an empirical rule (e.g., a rule that a difference occurs between a test result on a fine day and a test result on a rainy day) to be verified as data and be applied to calibration and a finer testing can be enabled.

A third aspect of the present invention relates to a testing system for performing testing. In the present invention, one or a plurality of testing apparatuses is connected to a testing system over a network, and a usage environment among the testing apparatuses is controlled. A testing system according to the present invention includes a database and a communication device. A table set downloaded from a wide area network is stored in the database. The testing apparatuses access the testing system and refer to tables stored in the testing system. The testing apparatuses update use conditions and result-correcting conditions in respective tables of the testing apparatuses, and then the apparatuses set use conditions and result-correcting conditions for testing elements. The communication device is connected to the wide area network. The testing system accesses respective remote servers prepared by vendors over the wide area network and it downloads table sets to be referred to by the testing apparatuses from the remote servers into the database. The testing system collects test results, use conditions, and pieces of information specific to the testing elements, such as a serial number specific to an element, from the testing apparatuses, and it complements the table sets stored in the database, with the collected pieces of information.

With the above-described configuration, the latest table sets can be constantly downloaded from the remote servers of the vendors, and if a defective product (unusable lot) is found, information indicating, e.g., discontinuance of use of a corresponding testing element can be acquired and be distributed to the testing apparatuses. The testing system can also share information with a testing system connected over the wide area network and perform subsequent tests with higher accuracy, by statistically processing pieces of information collected from the testing apparatuses and uploading the pieces of information to the network. The testing system can also constantly update and improve target test items based on the latest information by connecting to the remote servers prepared by the vendors.

First Embodiment

A first embodiment of the present invention will be described below with reference to FIGS. 1 to 4.

The present embodiment is directed to a test using a reaction in which the amount of fluorescence in a reagent is changed by introducing the reagent into a fine channel fluid path and continuously heating the reagent. As a method for continuously heating the reagent, a heater metal which produces heat is brought into contact with the channel fluid path containing the introduced reagent through a protective film. This enables prompt and stable heating. By using platinum as the material for the heater which produces heat, the temperature of the heating element is detected, by and measuring a value of resistance of the heater, according to a physical constant. Accordingly, the relationship between the temperature of the reagent and the amount of fluorescence produced and measured at the temperature can be known.

Figure 2:
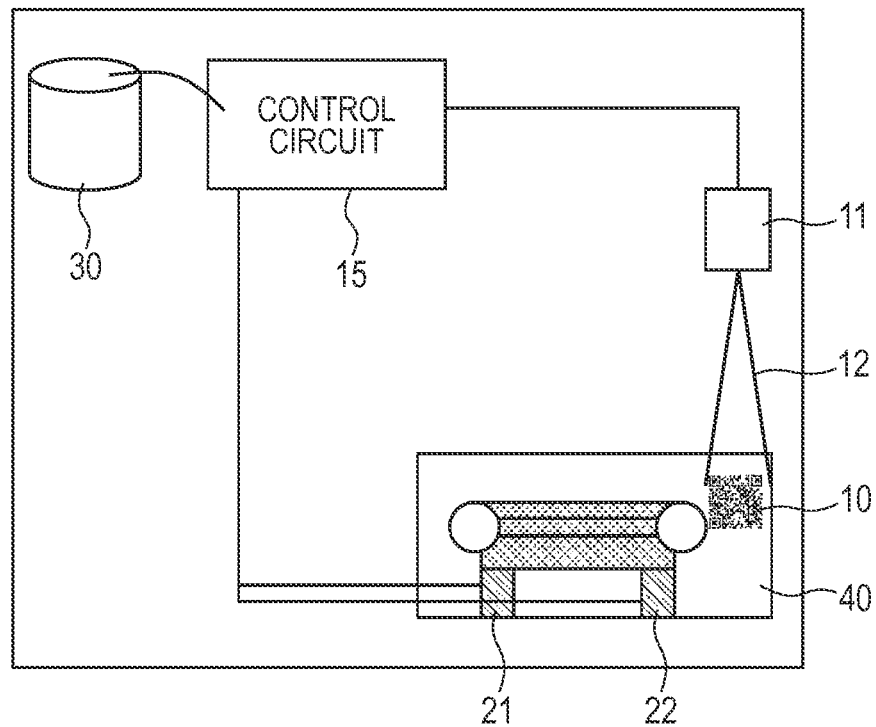
FIG. 2 illustrates a testing apparatus according to the first embodiment of the present invention.

FIG. 1 illustrates a testing element 40 used in the present embodiment. FIG. 2 illustrates a testing apparatus 51 used in the present embodiment.

In the testing element 40, a reagent is introduced through a reagent inlet 1 and discharged through a reagent outlet 2. A pump (not shown) is connected to the reagent outlet 2. A negative pressure is generated by the pump to suck the reagent. The reagent moves through a channel fluid path 3 in contact with a heater electrode 4. The reagent in the channel fluid path 3 is heated by the heater electrode 4 when the heater electrode 4 is powered through wiring electrodes 5(a) and 5(b).

A value of resistance used throughout the system of the heater electrode 4 is recorded in an information recording section 10, and information in the information recording section 10 is taken out from the information recording section 10 by a reading apparatus 11. The reading apparatus 11 emits detection light 12 and acquires the information recorded in the information recording section 10 by using reflected return light.

In the present embodiment, manufacturing process errors of individual testing elements generated during a testing element manufacturing process are measured. An item to be measured is a value of resistance. A process factor makes testing elements different in film thickness and the total amount of metal and thus it causes the test elements to have deviated values of resistance. A value of resistance also varies depending on the state of contact with a wiring metal.

The amount of heat generated by input power varies with a change in a value of resistance in a testing element. To maintain a certain rate of temperature rise, power input to a heater metal which is arranged for each channel and which is in contact with the channel needs to be changed according to a deviation of the value of resistance of the heater metal. When a value of resistance in a testing element varies, an error occurs in a temperature to be measured. For this reason, values of resistance of respective channel fluid paths are measured in advance for each of testing elements, and the values are recorded on the surface of the testing element using a QR Code (registered trademark) or a bar code. Simultaneously, a manufacturing plant and the date and time of manufacture are recorded as information on characteristics of the testing element. Although an example using a QR Code (registered trademark) or a bar code as a commonly used unit is described herein, information may be recorded using a non-contact semiconductor memory device, such as an RF-IC or a FeliCa (registered trademark), and may be read out in a non-contact wireless manner. A unit suitable for each case can be adopted in view of the balance between the amount of information used and the cost of a testing element.

The testing element 40 is set in the testing apparatus 51. Simultaneously, a QR Code (registered trademark) or a bar code is read with an infrared reader, and recorded information is passed as a use condition value to the testing apparatus. The testing apparatus refers to a table based on the read-out use condition value and it sets a use condition and a result-correcting condition.

In the testing apparatus 51 in FIG. 2, information recorded in the information recording section 10 is taken out by the reading apparatus 11 and it is passed to a control circuit 15. The control circuit 15 causes a wiring electrode (a) 21 and a wiring electrode (b) 22 to input power based on the passed information.

A condition under which the testing element 40 is used and a result are recorded in a data record 30. A use condition for the testing element 40 with even fewer errors can be calculated by statistically processing such results.

The testing apparatus 51 stores a test type, a reagent used, a use date and time, the serial number of an element, and the like as data in the data record 30 together with a test result. The testing apparatus 51 statistically processes a result of performing a test based on a use condition and a result-correcting condition recorded in and read out from each testing element and saves items necessary for a test, such as test type, reagent type, and the amount of reagent. the elapsed time to use can be calculated from a manufacture date and a use date, and it can be used to calibrate a result considering a change with time. Accumulated data can be promptly fed back when a testing element is used next time, and a similar test can be more efficiently performed.

The testing apparatus 51 may measure the temperature, humidity, and atmospheric pressure of the installation environment of the apparatus, vibrations around the apparatus, and the like by using a thermometer, a hygrometer, and a vibration sensor and store the data together with a test result. In this case, establishment of an environment which can verify, as data, an empirical rule (e.g., a rule that a difference occurs between a test result on a fine day and a test result on a rainy day) enables finer testing.

Figure 3:
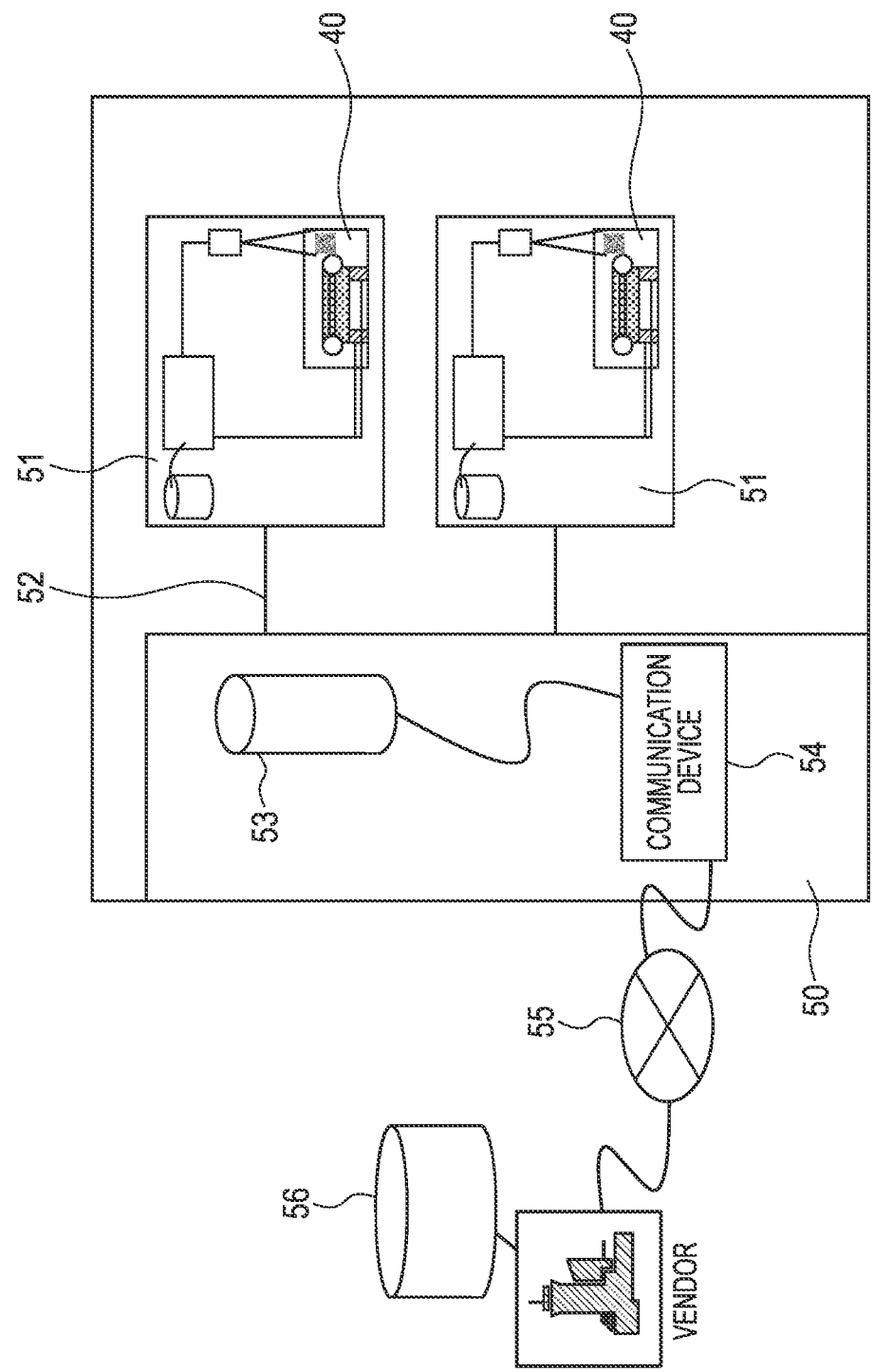
FIG. 3 illustrates a testing system according to the first embodiment of the present invention.
Figure 4:
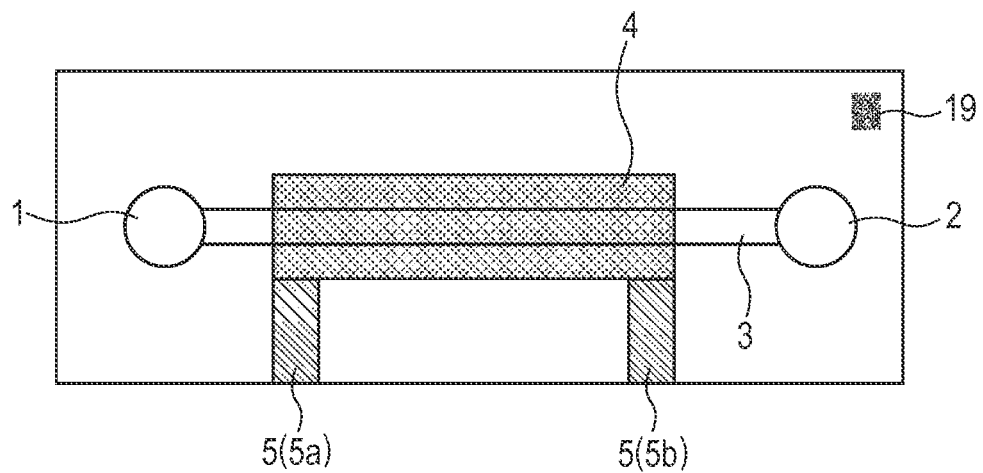
FIG. 4 illustrates another testing element according to the first embodiment of the present invention.

In a testing system in FIG. 3, a testing system 50 is connected to one or a plurality of testing apparatuses 51 over a network 52. The testing system 50 includes a database 53 and a communication device 54, and the communication device 54 is connected to a wide area network 55. The testing system 50 controls a usage environment among the plurality of testing apparatuses 51. For example, the testing system 50 distributes table sets (which may be part or the whole of a table) to be referred to the testing apparatuses and updates items to be referred to in a table in each testing apparatus. The testing system 50 also collects pieces of information specific to testing elements, such as test results, use conditions, result-correcting conditions, and the serial number of an element, from the testing apparatuses, and complements the table sets with the collected pieces of information. The testing system accesses respective remote servers 56 (which are connectable over a network) prepared by vendors to download the latest data table sets. If a defective product (unusable lot) is found, the testing system acquires information indicating, e.g., discontinuance of use of a corresponding testing element and distributes the information to the testing apparatuses. The testing system collects use information and result-correcting conditions from each testing apparatus, statistically processes the use condition and result-correcting condition of each testing element of each testing apparatus, and shares information with a testing system connected over a network such that subsequent tests can be performed with higher accuracy. The testing system can update and improve target test items by connecting to the remote servers prepared by the vendors.

In this embodiment, the present invention has been described as use of a QR Code (registered trademark). However, even if a semiconductor chip, such as an RF-IC, which wirelessly reads out information is embedded in an information recording section 19, as illustrated in, e.g., FIG. 4, information, such as a use condition, which is associated with use of a testing element, can be read out.

Second Embodiment

A second embodiment of the present invention will be described below with reference to FIG. 5.

The present embodiment relates to a medical testing element, a medical testing apparatus, and a medical testing system, to which the present invention is applied. A medical testing element as referred to herein is typified by μ-TAS, and the term generally indicates elements used in medical test and diagnosis and the like, such as a DNA chip, a lab-on-a-chip, a microarray, and a protein chip.

The present embodiment will describe a medical test which performs testing by continuously introducing a reagent into a fine channel fluid path. Methods for continuously introducing a reagent include the process of sucking a reagent supplied to an inlet with, e.g., a pipet by using a suction unit, such as a pump or a syringe, and the process of pressure-feeding a reagent supplied to an inlet by using a pressurization unit, such as a syringe. Another available method includes the process of feeding a reagent by using ultrasonic waves or SAW (surface acoustic waves). The process of generating a negative pressure by using a pump and sucking a reagent by utilizing a pressure difference will be described here.

Introduction of a reagent into a fine channel fluid path requires control of a fine pressure. Generally, a dye or a fluorescent dye is introduced to make a reagent visible, and pressure is controlled while the state of the reagent in a channel fluid path is monitored, thereby sucking a desired amount of reagent and drawing the reagent to a desired position. If the state of the reagent is completely monitored, and the behavior of the monitored reagent is completely fed back for control of a pump, a desired amount of reagent can be drawn to a desired position. However, introduction of a stable amount of reagent and the process of promptly keeping a reagent at a desired position are difficult, due to a delay in a control feedback loop or the insufficient specifications of a monitor unit.

In such a case, the process of measuring the pressure resistance of each channel fluid path in advance and informing the medical testing apparatus side of a different pressure resistance for each medical testing element enables a desired reagent to be handled in a short time.

The pressure resistance of a channel fluid path results mainly from the dimensions (opening area) of the channel fluid path and surface roughness at an inner wall of the channel fluid path. There are several methods for forming a channel fluid path. Among them, a method for creating a channel fluid path using sand blast will be exemplified without limitation hereinafter.

A substrate is prepared, a resist material used in a semiconductor process is applied to the substrate, and a pattern is written by the method of, e.g., lithography. After an unnecessary part of the resist material is removed, a desired pattern is left. The pattern is used as a mask, and particulate glass beads are blasted all over the substrate at high speed. Due to the difference in hardness between the resist material and the material for the substrate, the substrate material is ground according to the written pattern, in which process microscopic asperities are unavoidably formed. By cleaning the resist material after a desired number of channel fluid paths are engraved, pattern fluid paths can be obtained while the substrate has a smooth surface. Another flat substrate is compression-bonded to the substrate with the engraved pattern fluid paths. If a glass material is used as the material for the substrates, and two surfaces to be bonded are processed so as to have ultra-smooth surfaces, both the substrates can be brought into optical contact and be bonded to each other at this time.

In the channel fluid paths thus formed, there are variations in the depths and forms of grooves formed by engraving as machining errors generated during sand blasting. Surface roughness may occur also at the surface of each formed groove depending on the particle diameter of a glass bead used in sand blasting. Generally, since a pattern for a plurality of channel fluid paths is formed in one substrate, and the plurality of channel fluid paths are cut off after being formed, 20 to 50 channel fluid paths for a testing element which are cut off from the same substrate are considered as being formed under relatively uniform conditions. Dimensions and surface roughness, however, may differ depending on, e.g., the blasting direction in sand blast. Testing elements which are cut off from another substrate are often different in the dimensions of a channel fluid path and surface roughness because the testing elements include a lot error.

Figure 5:
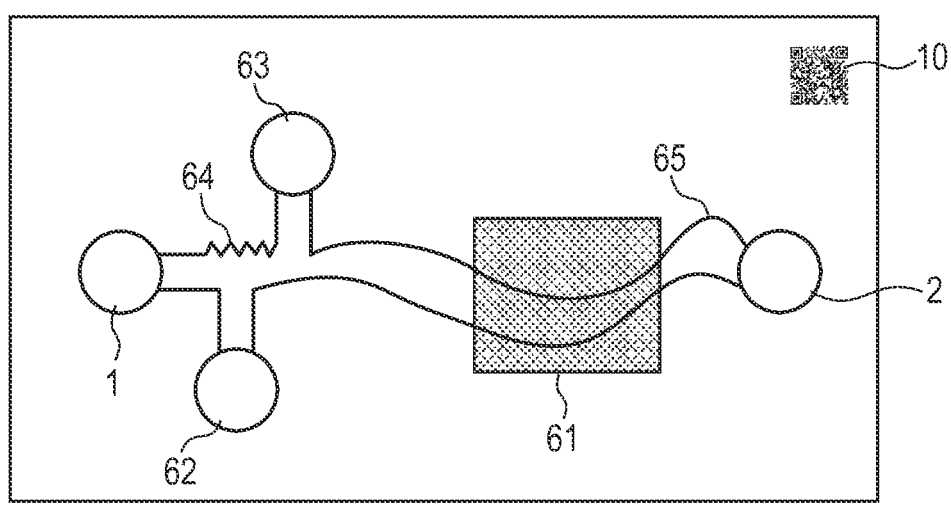
FIG. 5 illustrates a testing element according to a second embodiment of the present invention.

With reference to FIG. 5, which is a schematic view of a medical testing element 41 used in the present embodiment, a reagent is introduced through a reagent inlet 1 and reacts at a reaction section 61, while it is sucked by a pump (not shown) which is connected to a reagent outlet 2. A mixed reagent (a) 62 and a mixed reagent (b) 63 which are to react with the reagent for a test are arranged in a channel fluid path. Respective sections for the mixed reagents each include a unit configured to control pressure. Each section can mix an arbitrary amount of reagent into the channel fluid path.

The channel fluid path of the medical testing element 41 includes a form error 65 and surface roughness 64 which are generated during manufacture. The form error 65 and surface roughness 64 are responsible for non-uniformity in fluid path resistance throughout the element.

In addition to such a difference specific to each channel fluid path that is generated during a manufacturing process, effects of surface modification during a storage period are non-negligible. In a liquid reagent in a fine fluid path, the flow velocity near the surface of the fluid path is substantially zero, and a laminar flow is established. How a flow velocity difference is generated largely depends on the surface condition. Even a glass substrate of, e.g., quartz glass, is expected to suffer various effects, such as effects from ultraviolet rays, effects of exposure to air containing oxygen and carbon dioxide, and effects of dust adsorption during transport or during use. Surface modifications as described above cause variations in fluid path resistance.

Effects of a difference in fluid path resistance on control of a liquid reagent in a channel fluid path can be avoided by making the liquid reagent in the channel fluid path visible after setting of a testing element and changing a control parameter while monitoring the liquid. However, this requires a complicated mechanism, and desired control is difficult to achieve. An error generated during a manufacturing process can be avoided by measuring, in advance, channel dimensions, surface roughness, and the like and recording a measurement result in a medical testing element.

For this reason, for each medical testing element, the dimensions and surface roughness of each channel fluid path are measured in advance, and a value of fluid path resistance of each channel of the medical testing element is calculated from measured values. The calculated values of fluid path resistance are recorded in an information recording section 10 at the surface of the medical testing element by using a QR Code (registered trademark) or a bar code. Simultaneously, a manufacturing plant and the date and time of manufacture are recorded as pieces of information. The present embodiment describes an example using a QR Code (registered trademark) or a bar code as a commonly used unit. However, information may be recorded using a non-contact semiconductor memory device, such as an RF-IC or a FeliCa (registered trademark), and may be read out in a non-contact wireless manner.

The medical testing element 41 is set in a medical testing apparatus. Simultaneously, a QR Code (registered trademark) or a bar code is read with an infrared reader, and recorded information is passed as a use condition value to the medical testing apparatus. The medical testing apparatus refers to a table based on the read-out use condition value and sets a use condition and a result-correcting condition.

The medical testing apparatus 41 stores a test type, a reagent used, a use date and time, the serial number of an element, and the like as data together with a test result. The medical testing apparatus statistically processes a result of performing a test based on use conditions recorded in and read out from medical testing elements and saves items necessary for a test, such as test type, reagent type, and the amount of reagent. The elapsed time to use can be calculated from a manufacture date and a use date, and the information can be used to calibrate a result considering a change with time. Accumulated data can be promptly fed back when a testing element is used next time, and a similar test can be more efficiently performed.

The medical testing apparatus measures the temperature, humidity, and atmospheric pressure of the installation environment of the apparatus, vibrations around the apparatus, and the like and stores the data together with a test result. Establishment of an environment which can verify, as data, an empirical rule (e.g., a rule that a difference occurs between a test result on a fine day and a test result on a rainy day) enables finer testing.

A medical testing system controls a usage environment among a plurality of medical testing apparatuses. The medical testing system distributes table sets to be referred to the medical testing apparatuses and performs updating. The medical testing system also collects test results, use conditions and result-correcting conditions, and pieces of information specific to testing elements, such as the serial number of an element, from the medical testing apparatuses and complements the table sets with the collected pieces of information. The medical testing system accesses respective remote servers (which are connectable over a network) prepared by vendors to download the latest data table sets. If a defective product (unusable lot) is found, the medical testing system acquires information indicating, e.g., discontinuance of use of a corresponding medical testing element and distributes the information to the medical testing apparatuses. The medical testing system collects use information and result-correcting conditions from each medical testing apparatus, statistically processes the use condition of each medical testing element of each medical testing apparatus, and shares information with a testing system connected over a network such that subsequent tests can be performed with higher accuracy. The medical testing system can update and improve target test items by connecting to host servers prepared by vendors.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-100981, filed Apr. 28, 2011, which is hereby incorporated by reference herein in its entirety.

REFERENCE SIGNS LIST 1 reagent inlet
2 reagent outlet 3 channel fluid path
4 heater electrode
5(a) wiring electrode
5(b) wiring electrode
10 information recording section
11 reading apparatus
12 detection light
15 control circuit
19 another example of information recording section
21 wiring electrode (+)
22 wiring electrode (−)
30 data recording section
40 testing element
50 testing system
51 testing element
52 network
53 database
54 communication device
55 wide area network
56 remote server
61 reaction section
62 mixed reagent (a)
63 mixed reagent (b)
64 surface roughness in channel fluid path
65 form error in channel fluid path

The invention claimed is:

1. A testing element for performing a specimen test, comprising:
an information recording section installed at a surface of and/or inside the testing element;
a plurality of fluid paths; and
a plurality of heater electrodes for heating each interior of the fluid paths, wherein information on a characteristic of the testing element is stored in the information recording section, the information including, as pieces of information, characteristics of the respective fluid paths which include a pressure resistance or a value of heater electrode resistance, and
wherein the information on the characteristic is read-out to set a control parameter for performing the specimen test.

2. The testing element according to claim 1, wherein the information recording section is a one-dimensional and/or two-dimensional bar code.

3. The testing element according to claim 1, wherein the information recording section is a semiconductor chip which reads out information through wireless communication.

4. A testing apparatus for performing a specimen test, comprising:
The testing element according to claim 1;
a unit configured to read out information on the characteristic of the testing element stored in the information recording section installed at the surface of and/or inside the testing element;
a unit configured to set a control parameter of the testing element based on the read-out characteristic of the testing element; and
a unit configured to use the testing element by using the read-out control parameter of the testing element to perform the specimen test.

5. The testing apparatus according to claim 4, wherein each time the apparatus performs a specimen test, the apparatus saves a serial number specific to a testing element used, a control parameter used for the testing element, and an installation environment of the apparatus when the test is performed, together with a result of the test.

6. The testing apparatus according to claim 5, further comprising a unit configured to update a database of a testing system with a control parameter, based on a result of a test by a testing element passed from the testing apparatus, the serial number specific to the testing element used at the test, the control parameter used for the testing element, and the installation environment of the apparatus when the test is performed.

7. A testing system for performing a specimen test, comprising:
the testing apparatus according to claim 4;
a unit configured to access a database connected to the system over a network; and
a unit configured to download, from the database, a latest table set for referring to a control parameter used when a testing element used by the testing apparatus is used, based on a serial number specific to the testing element, and configured to pass a result to the testing apparatus.

8. The testing element according to claim 1, wherein the characteristics of the respective fluid paths are information obtained by measuring in advance how much a value obtained by the testing element deviates from a reference value.

9. The testing element according to claim 1, wherein the test element is an element for DNA analysis using PCR.

* * * * *